United States Patent
Wright, Jr. et al.

[11] Patent Number: 5,429,595
[45] Date of Patent: Jul. 4, 1995

[54] ARTERIAL SAFETY AIR DIVERTER

[76] Inventors: Fred G. Wright, Jr.; Glenda C. Wright, both of 4605 86th St., Lubbock, Tex. 79424

[21] Appl. No.: 974,994

[22] Filed: Nov. 12, 1992

[51] Int. Cl.$^6$ .............................. A61M 5/00
[52] U.S. Cl. ........................... 604/9; 604/4; 604/5; 210/188; 210/194
[58] Field of Search ............ 604/4, 5, 9; 210/188, 210/194

[56] References Cited

U.S. PATENT DOCUMENTS

| | | | |
|---|---|---|---|
| 2,252,687 | 8/1941 | Bassett . | |
| 2,872,298 | 2/1959 | Van Loenen . | |
| 3,599,659 | 8/1971 | Nuter et al. . | |
| 3,849,071 | 11/1974 | Kayser . | |
| 3,901,808 | 8/1975 | Bokros | 604/4 |
| 3,993,067 | 11/1976 | Schachet et al. | 604/9 |
| 4,344,777 | 8/1982 | Siposs . | |
| 4,606,365 | 8/1986 | Siposs . | |
| 4,622,032 | 11/1986 | Katsura et al. . | |
| 4,676,771 | 6/1987 | Henke . | |
| 5,192,439 | 3/1993 | Roth et al. | 604/4 |

OTHER PUBLICATIONS

American Omni Medical, Inc., "Silent Guard" ™ Ball Valve, Lot No. 90628; Cat No. SG-10.

*Primary Examiner*—Paul Prebilic
*Attorney, Agent, or Firm*—Popham, Haik, Schnobrich & Kaufman, Ltd.

[57] ABSTRACT

A safety air diverter for use in open-heart surgery comprises a perfusate chamber having an air outlet port in fluid communication with the interior of the perfusate chamber, a perfusate outlet port in fluid communication with the interior of the perfusate chamber opposite and in axial alignment with the air outlet port, and a perfusate inlet port in fluid communication with the interior of the perfusate chamber. A fluid containment and air exit line extends outwardly from the air outlet port, while a purge line provides fluid communication between the fluid containment and air exit line and the perfusate inlet port. A pressure responsive ball valve travels in a track in communication with and in axial alignment with the air outlet port, and selectively seats in an O-ring positioned in the air outlet port. The track can extend to and be in communication with the perfusate outlet port, with an O-ring also positioned adjacent the perfusate outlet port. A filter filters all fluid exiting the perfusate chamber through the perfusate outlet port. The longitudinal axis of the perfusate inlet port can be perpendicular to the longitudinal axis of the perfusate chamber longitudinal axis, or alternatively, the perfusate inlet port can extend tangentially from the perfusate chamber.

15 Claims, 3 Drawing Sheets

ARTERIAL SAFETY AIR DIVERTER

BACKGROUND OF THE INVENTION

1. Field of the Invention

The present invention relates to safety devices for use during open-heart surgery for preventing air from entering into the patient's circulatory system. More specifically, the invention relates to a safety air diverter which is placed on the positive side of the blood pump.

2. Related Art

Since the inception of pump supported surgery, the threat of catastrophic pump accidents has continued to plague both surgeons and perfusionist alike. Reed and Stafford, in their text *Cardiopulmonary By-Pass* (Surgimedics/TMP 2nd Ed. 1985), have reported that during the six year period from 1972 through 1977, the number of injuries or deaths resulting from accidents was a conservative 1 per 1000.

Even though there have been some improvements made since that time, there have been other factors that have off-set these improvements. Increased caseload, inexperience, and increased number of tasks and responsibilities imposed upon the perfusionist, and changes in technique and equipment, are but a few of the reasons that have resulted in increased risks of pump accidents.

The most dreaded and most common result of these accidents is the introduction of air into the extracorporeal circuit. The attention which the perfusionist must devote to his or her previously-mentioned increased duties has distracted the perfusionist from his or her primary responsibility of insuring a proper reservoir level. One can easily see how this has ultimately increased the risk of accidentally permitting air to enter the arterial line.

Besides the emptying of the reservoir, there are other ways that air can enter the arterial line, including an oxygenator falling from the holder; an arterial line parting from the connector on the negative side of the pump head; a crack in a connector on the negative side of the pump head; a rupture of the tubing inside the arterial pump head; or any other phenomenon that may allow air to be drawn into the negative side and ultimately finding its way inside the human body.

There have been several attempts made throughout the history of open-heart surgery to address this air emboli issue. Gas bubble detectors, low level sensors, arterial filters, and arterial bubble traps, are a few of the attempts at addressing this problem. One example of such a device is the SILENT GUARD TM ball valve (Catalog No. SG-10) sold by American Omni Medical, Inc. of Costa Mesa, Calif. This ball valve is used on the negative side of the pump and incurs all of the disadvantages of any device which might be utilized on the negative side. Reed and Stafford commented on this ball valve as follows in *Cardiopulmonary By-Pass*: "There is one ball type valve on the market which is placed in-line between the arterial outlet connector and the arterial pump head [i.e., on the negative side of the pump] .... There is some controversy over the effectiveness of this device from 100% fool-proof safe on the one hand to being able to pump air past the device in a low flow rate situation. Regardless, the following has been reported and can occur extremely rapidly: The arterial blood level is lost, the ball check valve engages, gas is cavitated out of the blood and in the arterial line between the oxygenator and the pump head, blood returned to the arterial reservoir disengages the check valve and the gas bubbles are pumped into the patient. We do not believe that this device is the answer to the problem."

Thus, even though these prior art devices have improved upon the safety aspects of extracorporeal surgery, they certainly have not eliminated the risks. Reed and Stafford state in *Cardiopulmonary By-Pass*: "These authors are at a loss to understand why more safety devices have not appeared on the market. Certainly, manufacturing has been told about the need for these devices for the past eight to ten years". It is the solution of this and other problems to which the present invention is directed.

SUMMARY OF THE INVENTION

It is therefore a primary object of the invention to provide a device for preventing the introduction of air into the arterial line during open heart surgery or any other procedure in which positive pressure is used to deliver blood or solution to the human body.

It is another object of the invention to provide a device for preventing the introduction of air into the arterial line during open heart surgery which can be placed on the positive side of a blood pump used during open heart surgery.

It is still another object of the invention to provide a device for preventing the introduction of air into the arterial line during open heart surgery which can be incorporated into the arterial filter used during open heart surgery.

It is still another object of the invention to provide a device for preventing the introduction of air into the arterial line during open heart surgery which can be integrated into the membrane oxygenator used during open heart surgery.

These and other objects of the invention are achieved by the provision of a safety air diverter for use in open-heart surgery which comprises a perfusate chamber having opposed outlet and inlet ends, an air outlet port in fluid communication with the interior of the perfusate chamber at the air outlet end, a perfusate outlet port in fluid communication with the interior of the perfusate chamber at the perfusate outlet end, and a perfusate inlet port in fluid communication with the interior of the perfusate chamber. A fluid containment and air exit line extends outwardly from the air outlet port, while a purge line provides fluid communication between the fluid containment and air exit line and the perfusate outlet port. The air inlet port is selectively opened and closed by a pressure responsive valve. A filter filters all fluid exiting the perfusate chamber through the perfusate outlet port.

In one aspect of the invention, the valve also selectively opens and closes the perfusate outlet port.

In another aspect of the invention, the air outlet port and the perfusate outlet port are coaxial with the longitudinal axis of the perfusate chamber.

In yet another aspect of the invention, the valve comprises an O-ring positioned in the air outlet port, a ball valve dimensioned for sealing engagement with the O-ring, and a track which defines a path of travel for the ball valve below the O-ring. The track can extend to and be in communication with the perfusate outlet port, with an O-ring also positioned in the perfusate outlet port.

In still another aspect of the invention, the longitudinal axis of the perfusate inlet port is perpendicular to the longitudinal axis of the perfusate chamber longitudinal axis. Alternatively, the perfusate inlet port extends tangentially from the perfusate chamber.

In still another aspect of the invention, the perfusate chamber includes a raised neck at the air outlet end, and the air outlet port extends outwardly from the raised neck.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
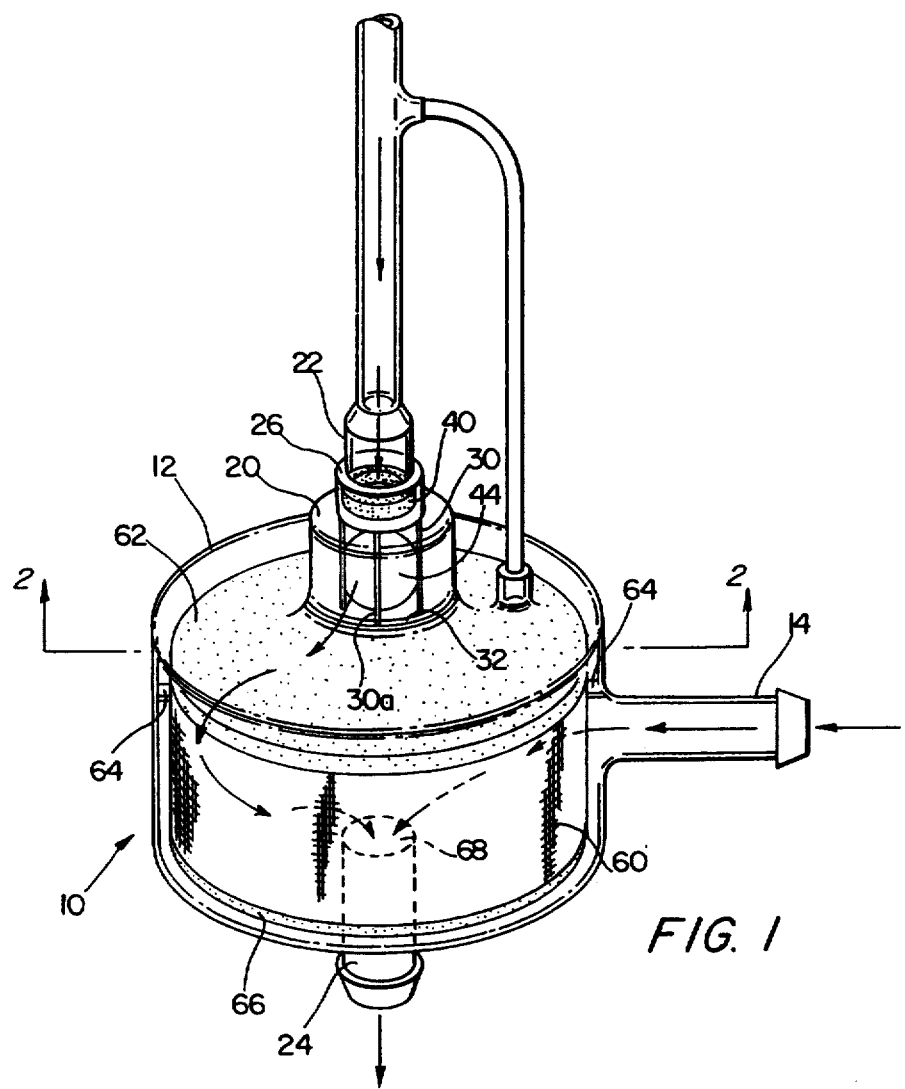
FIG. 1 is a perspective view of a first embodiment of an arterial safety air diverter in accordance with the present invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Figure 4:
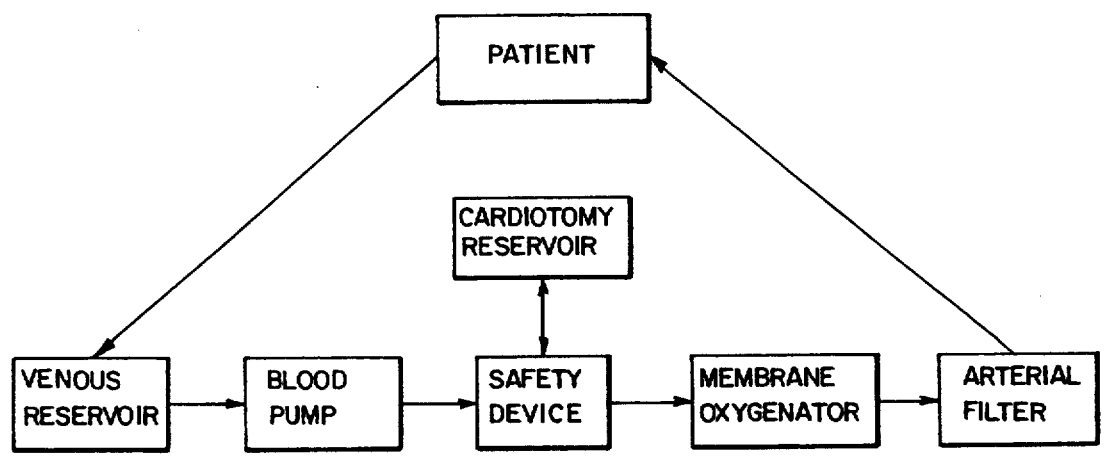
FIG. 4 is a flow chart illustrating placement of the arterial safety air diverter in accordance with the present invention between the pump head and the oxygenator.
Figure 5:
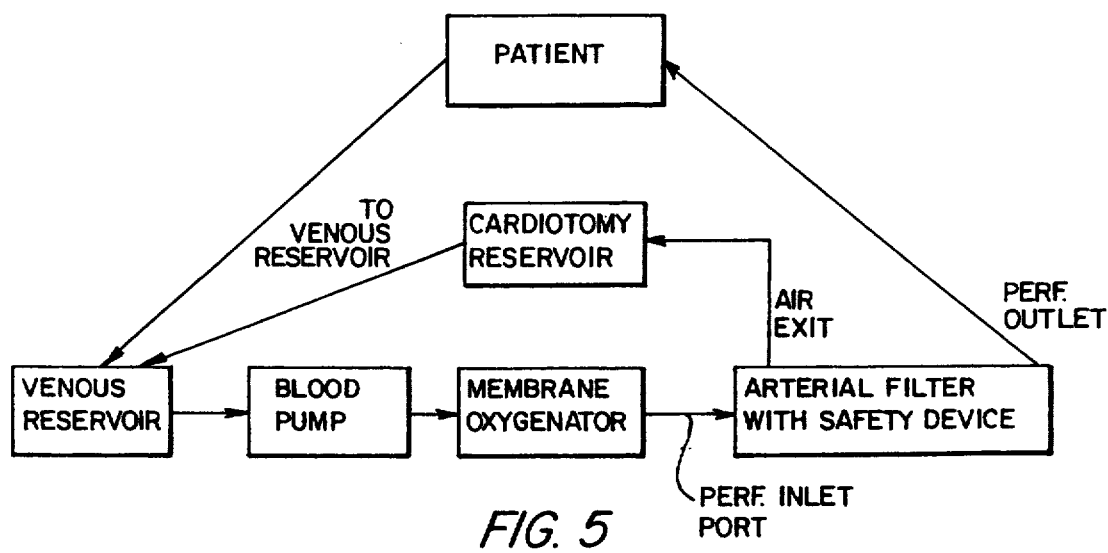
FIG. 5 is a flow chart illustrating placement of the arterial safety air diverter in accordance with the present invention between the oxygenator and the arterial cannula.
Figure 6:
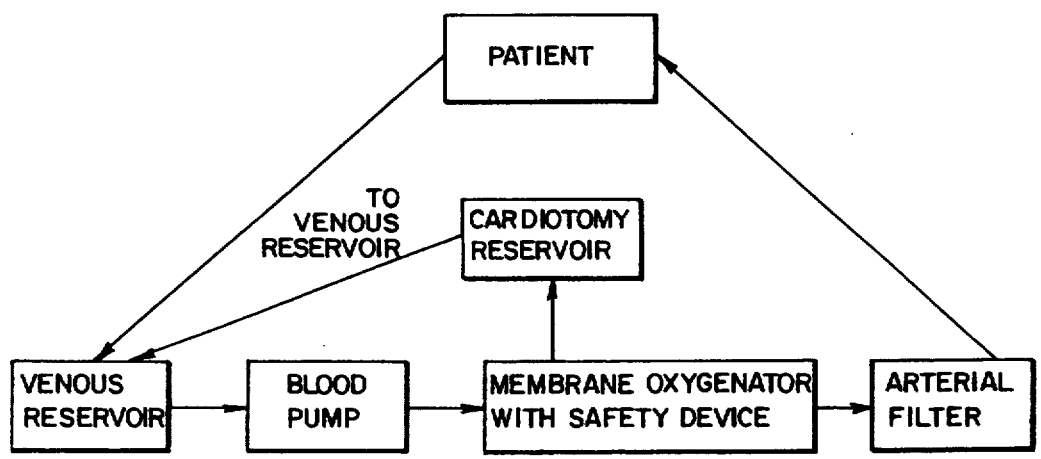
FIG. 6 is a flow chart illustrating integration of the arterial safety air diverter in accordance with the present invention into the membrane oxygenator on the inlet side.

A safety air diverter in accordance with the present invention is intended for use during applications of extracorporeal blood flow where the accidental introduction of air into the system is a hazard. The safety air diverter in accordance with the invention is placed on the POSITIVE side of the blood pump. Placement can be between the pump head and the oxygenator, as shown in FIG. 4, or between the oxygenator and the arterial cannula, as shown in FIG. 5. The safety air diverter can also be incorporated into the arterial filter and placed in the same location as shown in FIG. 5 or it can be integrated into the membrane oxygenator on the inlet side as shown in FIG. 6. The location of the safety air diverter will depend upon the particular application and desires of the open-heart team. Proper use of the safety air diverter in accordance with the invention will prevent air from accidentally entering the extracorporeal circuit should the venous reservoir accidentally be emptied.

Figure 7:
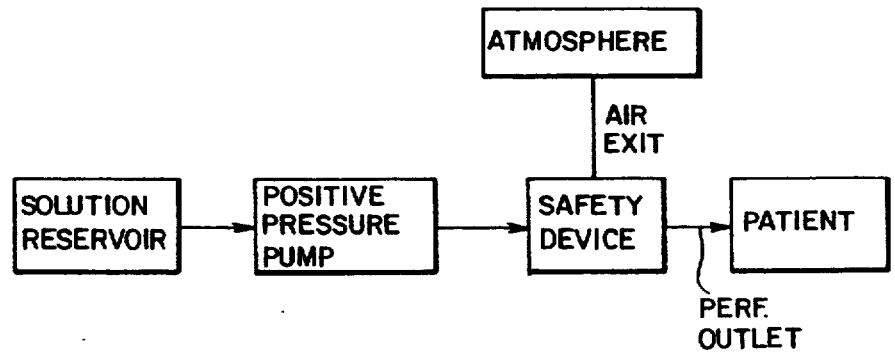
FIG. 7 is a flow chart illustrating placement of the arterial safety air diverter in accordance with the present invention during any procedure where positive pressure is being utilized to deliver blood or solution to the human body.

Although the safety air diverter in accordance with the invention is of particular usefulness in preventing air from accidentally entering the extracorporeal circuit should the venous reservoir accidentally be emptied, it is not limited to this application. The safety air diverter in accordance with the invention can be utilized during any procedure where positive pressure is being utilized to deliver blood or solution to the human body, as shown in FIG. 7.

The safety air diverter in accordance with the invention is also of benefit during cardioplegia applications, being used in the same manner as previously described to prevent air from accidentally entering the coronaries should the reservoir supplying the solution be accidentally emptied. In addition, the safety air diverter in accordance with the invention can be used as a safety device when infusing blood or solution into the body's venous system. A more detailed explanation of the structure of the safety air diverter in accordance with the invention is given below with reference to FIGS. 1 through 3.

Figure 2:
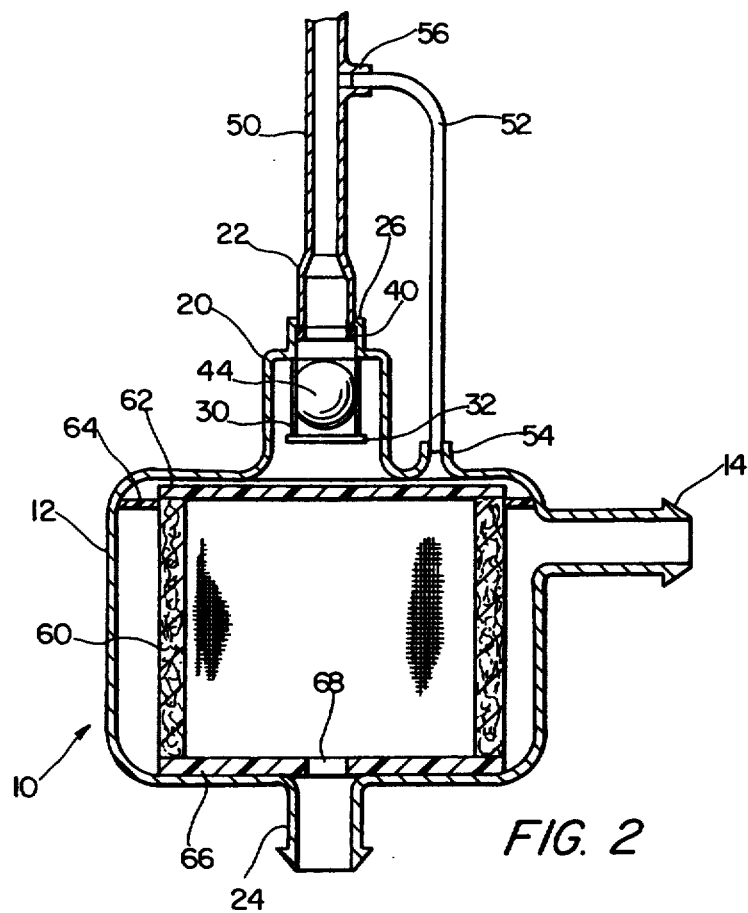
FIG. 2 is a cross-sectional view taken along line 2—2 of FIG. 1.

Referring now to FIGS. 1 and 2, there is shown a first embodiment of an arterial safety air diverter 10 in accordance with the present invention. Safety air diverter 10 includes a perfusate chamber 12 having a longitudinal axis, a perfusate inlet port 14 at one side thereof, a raised neck 20 having an air outlet port 22 extending therefrom at the top or air outlet end of perfusate chamber 12 coaxial with the longitudinal axis, and a perfusate outlet port 24 at the bottom or perfusate outlet end of perfusate chamber 12 coaxial with the longitudinal axis. Perfusate inlet port 14 and perfusate outlet port 24 are barbed at the end to retain silicone or other plastic or rubber tubing (not shown) under pressure situations.

As shown in FIGS. 1 and 2, perfusate inlet port 14 extends outwardly adjacent the top of perfusate chamber 12. The longitudinal axis of inlet port 14 can be perpendicular to that of perfusate chamber 12 (i.e., inlet port 14 can extend radially from perfusate chamber 12), or inlet port 14 can be tangential to perfusate chamber 12. Although a tangential arrangement is preferred, any angle is acceptable which does not hinder the dynamic function of the valve, as described in detail hereinafter.

The bottom of air outlet port 22 is necked-out at its junction with the top of raised neck 20 to define an upper collar 26. A valve containment track 30 extends from upper collar 26 into raised neck 20, coaxial with the longitudinal axis of perfusate chamber 12, and terminating at an annular lower collar 32 adjacent the bottom of raised neck 20. Track 30 can be formed by a plurality of longitudinal rods 30a formed integrally with raised neck 20.

Preferably, perfusate chamber 12, ports 14, 22, and 24, upper collar 26, track 30, and lower collar 32 are unitarily formed of a transparent polymer material, such as polycarbonate or a similar non-toxic material, which can readily be formed and which in use allows the perfusionist to view the interior of perfusate chamber 12.

An upper O-ring 40 is placed in upper collar 26. A ball valve 44 rides in track 30, with upper O-ring 40 functioning as a valve seat for ball valve 44. Ball valve 44 preferably is constructed of a semi-pliable material such as a semi-rigid silicone rubber or other non-toxic material which will allow for proper seating against O-ring 40. Likewise, O-rings 40 is formed of a non-toxic pliable rubber which will allow for effective seating and sealing of ball valve 44, that is, which is soft enough to seat and form a seal with ball valve 44, yet is rigid enough to prevent sticking of ball valve 44.

As will be appreciated by those of skill in the art, even though a ball valve generally would be the least likely to malfunction, other valve designs which function in a similar manner to ball valve 44 and O-ring 40 can be used. Examples of such valves include, but are not limited to mono-leaflet, bi-leaflet, and multi-leaflet disc valves, duck bill valves, or any other type of valve that would respond to differential pressure gradients.

A fluid containment/air exit line 50 extends outwardly from air outlet port 22 coaxial with the longitudinal axis of perfusate chamber 12. Fluid containment-/air exit line 50 is in fluid communication with perfusate inlet port 14 through a purge line 52 connected to perfusate inlet port 14 at a luer vent port 54 formed proximate the junction of perfusate inlet port 14 with the upper surface of perfusate chamber 12, and connected to fluid containment/air exit line 50 at an upper vent port 56 formed unitarily therein upwardly of air outlet port 22.

Purge line 52 is formed as a separate element from perfusate inlet port 14 and fluid containment/air exit line 50 and is removably connected thereto by conventional means. For example, luer vent port 54 and upper vent port 56 can be provided with internal threads and purge line 52 can be provided at both ends with mating external threads. Thus purge line 52 can easily be removed and/or replaced. Also, purge line 52 can be provided in different lengths.

A cylindrical filter 60 is positioned within perfusate chamber 12 and inset from the inner side surface of perfusate chamber 12. Preferably, filter 60 is a mesh constructed from polyester, but other non-toxic materials suitable for filtration can also be used.

A urethane cap 62 at the top of filter 60 is anchored to perfusate chamber 12 adjacent the air outlet end by a plurality of urethan pins 64. A urethane cap 66 at the bottom of filter 60 is sealed to the perfusate outlet end of perfusate chamber 12, and isolates the inflow from the outflow side. Cap 66 has an opening 68 therethrough in axial alignment with outlet 24, to permit outflow of the filtered perfusate. Caps 62 and 66 force all fluid entering perfusate chamber 12 to cross filter 60 in order to permeate to the outflow side.

Raised neck 20 reduces the priming volume of perfusate chamber 12 because the full width of the air outlet end of perfusate chamber 12 is not required to cause the valve to become operational. However, raised neck 20 is not essential to the operation of perfusate chamber 12, and in fact it can be omitted so that upper collar 26 is formed directly at the air outlet end of perfusate chamber 12. In either configuration of perfusate chamber 12, the priming volume should be maintained as low as possible, while at the same time offering enough volume to allow the valve to close and open properly. Perfusate chamber 12 can be configured to prime with as low a volume of solution as, for example, 10 cc. or as high a volume as, for example, 200 cc. The specific configuration of perfusate chamber 12, other than the inclusion or exclusion of raised neck 20, is primarily cosmetic in nature, provided the criteria for priming volume are met.

Preferred sizes for the various elements of safety air diverter 10 are as follows:

| Component | Size |
| --- | --- |
| Perfusate inlet port 14 | ¼ to ½ inch I.D. |
| Air outlet port 22 | ¼ to ½ inch I.D. |
| Perfusate outlet port 24 | ¼ to ⅜ inch I.D. |
| Ball valve 44 | ≈ ½ inch diameter |
| Air exit line 50 | 3/16 to ⅜ inch I.D. |
| Purge line 52 | 1/32 to 1/16 inch I.D. |
| Luer vent port 54 | 1/16 to 1/8 inch I.D. |
| Filter 60 | 25 to 40 microns |

As will readily be understood by those of skill in the art, port orientation, size, and arrangement can be varied according to the particular application, and should not be considered to be limited to the configurations and sizes shown and described.

Figure 3:
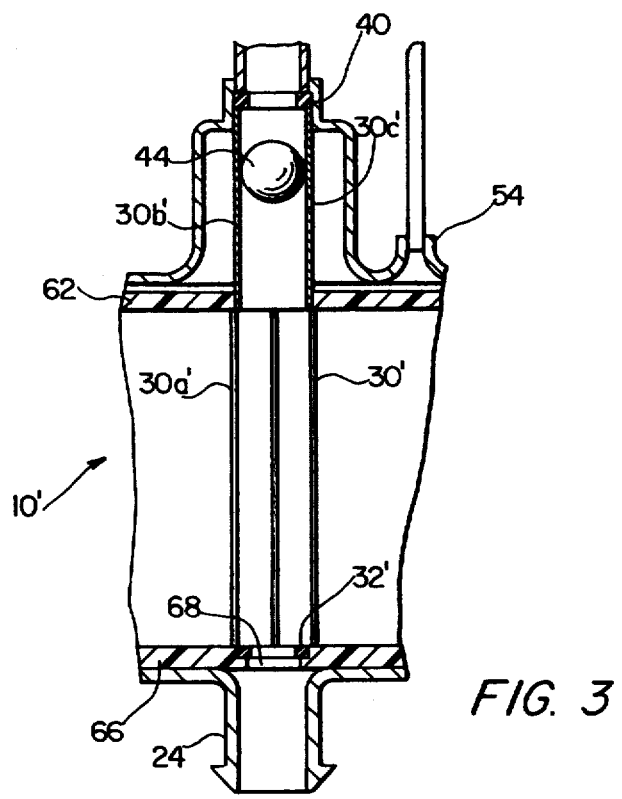
FIG. 3 is a cross-sectional view of an alternate embodiment of an arterial safety air diverter in accordance with the present invention.

Referring now to FIG. 3, there is shown an alternate embodiment of an arterial safety air diverter 10' in accordance with the present invention. Safety air diverter 10' is generally similar to safety air diverter 10 except for the configuration of the valve containment track 30'. In safety air diverter 10' track 30' extends from air outlet port 20 to perfusate outlet port 24.

Track 30' includes between top urethane cap 62 and bottom urethane cap 66 a plurality of longitudinal rods 30a' terminating at an O-ring 32' positioned in opening 68 in bottom urethane cap 66. Track 30' further includes a cylindrical polycarbonate chamber 30b' extending from air outlet port 20 to top urethane cap 62. Chamber 3b' and rods 30a' can be formed integrally.

Chamber 30b' has a sufficiently wide diameter to permit ball valve 44 to float freely therein, and preferably is transparent to enable ball valve 44 to be visible. A small hole 30c' is formed through the side wall of chamber 30b' to allow for venting to the pressure inside chamber 30b' to equalize with the pressure outside chamber 30b'. Hole 30c' must be sufficiently large to permit venting, but be sufficiently small to prevent any significant flow cross-over.

Track 30' is open on the outflow side at bottom urethane cap 66 to allow fluid to come into full contact with the perfusate solution. O-ring 32' permits ball valve 44 to seat, should perfusate solution be emptied to bottom urethane cap 66.

As previously indicated, the safety air diverter 10 and 10' should be placed on the positive side of the pump head. This placement can either be between the venous reservoir and the oxygenator, as shown in FIG. 4, or between the oxygenator and the arterial cannula, as shown in FIG. 5. It can also be incorporated inside the arterial filter which is already in the arterial line, as also shown in FIG. 5. The key point is that IT MUST BE USED ON THE POSITIVE SIDE OF THE PUMP HEAD IN ORDER TO BE EFFECTIVE.

Safety air diverter 10 and 10' is intended to prevent air from accidentally being introduced into the arterial line during cardiopulmonary by-pass. With reference to FIG. 5, this object is achieved in use as follows:

Safety air diverter 10 or 10' is connected in place in the extracorporeal circuit as shown in FIG. 5, using conventional tubing. The venous reservoir is initially primed. A clamp will be placed on the tubing on the outflow side of safety air diverter 10 or 10' i.e. at perfusate outlet port 24. Filling of the perfusate chamber 12 of safety air diverter 10 or 10' will begin as solution enters. The air inside perfusate chamber 12 will be displaced and forced out both luer port 54 and air outlet port 22.

When perfusate rises enough to come in contact with ball valve 44, ball valve 44 will float until safety air diverter 10 or 10' is completely primed. Simultaneously, ball valve 44 will come in contact with upper O-ring 40. Ball valve 44 will seal against O-ring 40 via positive pressure and prevent any additional flow through air outlet port 22. As this occurs, secondary flow will then begin to exit through luer port 54 and be transported upward to empty into fluid containment/air exit line 50. Solution will begin to fill fluid containment/air exit line 50 distal to ball valve 44 and O-ring seal 26. Overflow from the continuous purge will then be transported back to the cardiotomy reservoir and ultimately will be returned to the extracorporeal circuit.

During this continuous purge, a column of fluid will be maintained in fluid containment/air exit line 50 above and distal to ball valve 44 and O-ring seal 26. The height of this column will be based on the weight necessary to obtain ideal dynamic function. Even though a column of fluid should offer the lowest risk of malfunction, other mechanical means of continued resistance can be utilized. Such mechanical means includes, but is not limited to mechanical spring devices or any other device that can offer resistance and allow opening of the valve as solution empties in perfusate chamber 12.

The clamp will then be released from the vicinity of perfusion outlet port 24 and the remainder of the extracorporeal circuit will be primed. Safety air diverter 10 or 10' will then perform as follows:

During routine perfusion, the pressure inside perfusate chamber 12 will allow for ball valve 44 to be completely seated against O-ring valve seat 26 and routine perfusion will be maintained.

Should the venous reservoir accidentally be emptied both air and solution will enter inlet port 14. Loss of positive pressure will be obtained by the continual venting through luer port 54, which is connected to fluid containment/air exit line 50 through purge line 52 and will purge above the column of fluid and be vented to atmosphere via the cardiotomy reservoir. Even though this type of venting through purge line 52 seems to be the safest way to neutralize the pressure, other means can be used. For example, any means that would allow continuous purging and ultimate depressurization of the perfusate chamber could be utilized in safety air diverter 10 or 10'. As air enters perfusate chamber 12, the pressure inside will become neutralized and atmospheric. When this occurs, the weight being generated by the column of fluid inside fluid containment/air exit line 50 will cause ball valve 44 to fall to the bottom of track 30 or 30'. The solution in fluid containment/air exit line 50 will then empty into perfusate chamber 12, and fluid containment/air exit line 50 will become completely void of solution. Any air that enters perfusate inlet port 14 will then be transported via fluid containment/air exit line 50 to the cardiotomy reservoir and ultimately be vented to atmosphere. As additional air is pumped into perfusate chamber 12, it will be forced out to the atmosphere through fluid containment/air exit line 50 via air outlet port 22 and continually be purged into the cardiotomy reservoir.

Synergistically, the pressure being generated from the patient (arterial cannulation sight) will also be greater than atmospheric and will force the blood from the patient backwards and will ultimately purge air from safety air diverter 10. Ball valve 44 will once again seat against O-ring 40, establish pressure inside perfusate chamber 12, and establish flow.

Perfusate will once again fill the venous reservoir. It will be pumped in through inlet port 14, seat ball valve 44, and once again generate a positive pressure. By-pass will then be re-initiated.

Again, the key factor here is the positive pressure and the positive pressure valve, which as shown herein is a ball valve. However, as indicated above, the positive pressure valve can be a ball valve, a disc valve, or any other type of valve that will allow the system to close and open in accordance with the requirements of the invention. Regardless of the size or the shape, the valve should be of the proper weight so as not to be forced shut by air but, at the same time, be forced shut by solution.

When placed as shown in FIG. 4 or FIG. 6, the safety air diverter in accordance with the present invention is not used in its entirety. Rather, only raised neck 20, air outlet port 22, valve containment track 30, ball valve 44, fluid containment/air exit line 50, purge line 52, luer vent port 54, and upper vent port 56 are required. Preferably, inlet port 14, perfusate outlet port 24, filter 60, and polyurethane caps 62 and 66 would not be required or utilized.

The safety air diverter according to the invention should be designed with minimal priming volume but should be large enough to activate valve closure, and at the same time, allow air to exit.

Modifications and variations of the above-described embodiments of the present invention are possible, as appreciated by those skilled in the art in light of the above teachings. For example, it can be designed to any shape and configuration that would be conducive for proper utilization of the positive pressure valve. Moreover, the safety air diverter according to the invention will be beneficial in extracorporeal perfusion, cardioplegia applications, venous blood or solution infusion, or any application where air entering the body might be a hazard.

It is therefore to be understood that, within the scope of the appended claims and their equivalents, the invention may be practiced otherwise than as specifically described.

What is claimed is:

1. A safety air diverter for use in open-heart surgery, comprising:
   a perfusate chamber having a longitudinal axis, an interior, an air outlet end, and a perfusate outlet end opposite said air outlet end;
   an air outlet port in fluid communication with said interior of said perfusate chamber at said air outlet end, said air outlet port being coaxial with said longitudinal axis;
   a perfusate outlet port in fluid communication with said interior of said perfusate chamber at said perfusate outlet end, said perfusate outlet port being coaxial with said longitudinal axis;
   a perfusate inlet port in fluid communication with said interior of said perfusate chamber;
   a fluid containment and air exit line extending outwardly from said air outlet port;
   a purge line providing fluid communication between said fluid containment and air exit line and said perfusate inlet port;
   valve means for selectively opening and closing at least said air outlet port, said valve means comprising an O-ring positioned in said air outlet port and an O-ring positioned adjacent said perfusate outlet port, a ball valve dimensioned for sealing engagement with said O-rings, and track means for defining a path of travel for said ball valve between said O-ring positioned in said air outlet port and said O-ring positioned in said perfusate outlet port; and filter means for filtering all fluid exiting said perfusate chamber through said perfusate outlet port.

2. The safety air diverter of claim 1, wherein said valve means also selectively opens and closes said perfusate outlet port.

3. A safety air diverter for use in open-heart surgery, comprising:

a perfusate chamber having an interior, an air outlet end, and a perfusate outlet end opposite said air outlet end;

an air outlet port in fluid communication with said interior of said perfusate chamber at said air outlet end;

a perfusate outlet port in fluid communication with said interior of said perfusate chamber at said perfusate outlet end;

a perfusate inlet port in fluid communication with said interior of said perfusate chamber;

a fluid containment and air exit line extending outwardly from said air outlet port;

a purge line providing fluid communication between said fluid containment and air exit line and said perfusate inlet port;

valve means for selectively opening and closing at least said air outlet port;

filter means for filtering all fluid exiting said perfusate chamber through said perfusate outlet port; and a luer vent port in said air outlet end, said luer vent port being in fluid communication with said perfusate inlet port, and said purge line being connected at one end to said luer vent port and at said other end to said air exit line.

4. A safety air diverter for use in open-heart surgery, comprising:

a perfusate chamber having an interior, an air outlet end, and a perfusate outlet end opposite said air outlet end;

an air outlet port in fluid communication with said interior of said perfusate chamber at said air outlet end;

a perfusate outlet port in fluid communication with said interior of said perfusate chamber at said perfusate outlet end;

a perfusate inlet port in fluid communication with said interior of said perfusate chamber;

a fluid containment and air exit line extending outwardly from said air outlet port;

a purge line providing fluid communication between said fluid containment and air exit line and said perfusate inlet port;

valve means for selectively opening and closing at least said air outlet port; and filter means for filtering all fluid exiting said perfusate chamber through said perfusate outlet port, said filter means comprising a cylindrical filter having top end and a bottom end, a top urethane cap covering said top end of said filter and spaced from said air outlet end of said perfusate chamber, and a bottom urethane cap at said bottom end of said filter and in contact with said perfusate outlet end of said perfusate chamber, said bottom urethane cap having an aperture therethrough at said perfusate outlet port, wherein said top urethane cap has a central aperture therethrough, and wherein said valve means comprises an upper O-ring positioned in said air outlet port, a lower O-ring positioned at said aperture in said bottom urethane cap, a ball valve dimensioned for sealing engagement with said upper and lower O-rings, and track means for defining a path of travel for said ball valve between said upper and lower O-rings.

5. A safety air diverter for use in open-heart surgery, comprising:

perfusate chamber means for receiving a perfusate, said perfusate chamber means having a longitudinal axis;

air outlet port means for venting air from said perfusate chamber means, said air outlet port means being coaxial with said longitudinal axis;

perfusate outlet port means for exhausting the perfusate from said perfusate chamber means, said perfusate outlet port being coaxial with said longitudinal axis;

perfusate inlet port means for introducing perfusate into said perfusate chamber means;

fluid containment line means extending outwardly from said air outlet port means for containing a column of fluid above said air outlet port means;

purge means for continuously purging air from said perfusate chamber means and for depressurizing said perfusate chamber means;

valve means for selectively opening and closing at least said air inlet port means, said valve means comprising a valve seat positioned in said air outlet port means, a pressure-responsive valve movable into and out of engagement with said valve seat, and track means for defining a path of travel for said valve between said valve seat positioned in said air outlet port means and said perfusate outlet port means; and filter means for filtering all fluid exiting said perfusate chamber through said perfusate outlet port.

6. The safety air diverter of claim 3, wherein said perfusate chamber has a longitudinal axis, and wherein said air outlet port and said perfusate outlet port are coaxial with said longitudinal axis.

7. The safety air diverter of claim 6, wherein said valve means comprises an O-ring positioned in said air outlet port, a ball valve dimensioned for sealing engagement with said O-ring, and track means for defining a path of travel for said ball valve between said O-ring positioned in said air outlet port and a position below said air outlet port.

8. The safety air diverter of claim 7, wherein said valve means further comprises an O-ring positioned adjacent said perfusate outlet port, and wherein said track means defines a path of travel for said ball valve between said O-ring positioned in said air outlet port and said O-ring positioned in said perfusate outlet port.

9. The safety air diverter of claim 6, wherein said perfusate inlet port has a longitudinal axis, and wherein said perfusate inlet port longitudinal axis is perpendicular to said perfusate chamber longitudinal axis.

10. The safety air diverter of claim 6, wherein said perfusate inlet port extends tangentially from said perfusate chamber.

11. The safety air diverter of claim 1, wherein said perfusate chamber includes a raised neck at said air outlet end, and wherein said air outlet port extends outwardly from said raised neck.

12. The safety air diverter of claim 1, wherein said filter means comprises a cylindrical filter having top end and a bottom end, a top urethane cap covering said top end of said filter and spaced from said air outlet end of said perfusate chamber, and a bottom urethane cap at said bottom end of said filter and in contact with said perfusate outlet end of said perfusate chamber, said bottom urethane cap having an aperture therethrough at said perfusate outlet port.

13. The safety air diverter of claim 12, wherein said top urethane cap is solid, and wherein said valve means comprises an O-ring positioned in said air outlet port, a ball valve dimensioned for sealing engagement with said O-ring, and track means for defining a path of travel for said ball valve between said O-ring positioned in said air outlet port and a position below said air outlet port and above said top urethane cap.

14. The safety air diverter of claim 5, wherein said valve means also selectively opens and closes said perfusate outlet port means.

15. The safety air diverter of claim 5, wherein said valve means further comprises a valve seat positioned in said perfusate outlet port means, and wherein said track means defines a path of travel for said valve between said valve seat positioned in said air outlet port means and said valve seat positioned in said perfusate outlet port means.

* * * * *